US008426180B2

(12) United States Patent
Bergmann et al.

(10) Patent No.: US 8,426,180 B2
(45) Date of Patent: Apr. 23, 2013

(54) USE OF CARBAMOYL PHOSPHATE SYNTHETASE 1 (CPS) AS A HUMORAL BIOMARKER FOR THE DIAGNOSIS OF TUMOUR DISEASES AND CHRONIC INFLAMMATORY INTESTINAL DISEASES

(75) Inventors: Andreas Bergmann, Berlin (DE); Joachim Struck, Berlin (DE)

(73) Assignee: B.R.A.H.M.S GmbH, Henningsdorf (DE)

( * ) Notice: Subject to any disclaimer, the term of this patent is extended or adjusted under 35 U.S.C. 154(b) by 0 days.

(21) Appl. No.: 12/986,385

(22) Filed: Jan. 7, 2011

(65) Prior Publication Data

US 2012/0077208 A1 Mar. 29, 2012

Related U.S. Application Data

(63) Continuation of application No. 11/575,603, filed as application No. PCT/EP2005/009827 on Sep. 13, 2005, now abandoned.

(30) Foreign Application Priority Data

Sep. 21, 2004 (DE) .......................... 10 2004 045 705

(51) Int. Cl.
*C12Q 1/00* (2006.01)
*C12P 21/06* (2006.01)
*G01N 33/53* (2006.01)
*G01N 33/563* (2006.01)

(52) U.S. Cl.
USPC ................. 435/194; 435/4; 435/7.6; 435/7.9; 424/94.1; 424/9.1

(58) Field of Classification Search .................. None
See application file for complete search history.

(56) References Cited

U.S. PATENT DOCUMENTS

| 4,822,733 | A | 4/1989 | Morrison |
| 5,512,493 | A | 4/1996 | Mathis et al. |
| 5,639,617 | A | 6/1997 | Bohuon |
| 2004/0180396 | A1 | 9/2004 | Bergmann et al. |

FOREIGN PATENT DOCUMENTS

| EP | 0656121 | 4/1998 |
| EP | 1403282 | 3/2004 |
| WO | 99/63067 | 12/1999 |
| WO | 0073322 | 12/2000 |
| WO | 03/042661 | 5/2003 |
| WO | 03/089933 | 10/2003 |

OTHER PUBLICATIONS

Liu T-H et al., "Carbamyl Phosphate Synthetase I A Novel Marker for Gastric Carcinoma", Chinese Medical Journal, vol. 102(8), 1989, 630-638.
Lawson et al., "Urea synthesis in Novikoff and Morris hepatomas", Cancer Research 1977, vol. 37(3), 850-856.
International Search Report corresponding to PCT/EP2005/009827.
Ardawi, M.S.M., "Hepatic Glutamine Metabolism in the Septic Rat", Clinical Science (London)., 1992, vol. 82(6), 709-716.
Assicot et al., "High Serum Procalcitonin Concentrations in Patients with Sepsis and Infection", The Lancet, 1993, vol. 341(8844), 515-518.
Beishuizen et al., "Endogenous Mediators in Sepsis and Septic Shock", Advances in Clinical Chemistry, 1999, vol. 33, 55-131.
Gabay et al., "Acute-Phase Proteins and Other Systemic Responses to Inflammation", The New England Journal of Medicine, 1999, vol. 340(6), 448-454.
Ghillani et al., "Monoclonal Antipeptide Antibodies as Tools to Dissect Closely Related Gene Products", Journal of Immunology, 1988, vol. 141(9), 3156-3163.
Ghillani et al., "Identification and Measurement of Calcironin Precursors in Serum of Patients with Malignant Diseases", Cancer Research, 1989, vol. 49, 6845-6851.
Klose, J., "Fractionated Extraction of Total Tissue Proteins from Mouse and Human for 2-D Electrophoresis", Molecular Biology, vol. 112, 67-85.
Klose, J., "Two-dimensional Electrophoresis of Proteins: An Updated Protocol and Implications for a Functional Analysis of the Genome", Electrophoresis, 1995, vol. 15, 1034-1059.
Linger et al., "Reverse Transcriptase Motifs in the Catalytic Subunit of Telomerase", Science, 1997, vol. 276, 561-567.
Mann et al., "Use of Mass Spectrometry-Derived Data to Annotate Nucleotide and Protein Sequence Databases", Biochemical Sciences, 2001, vol. 26(1), 54-61.
Neubauer et al., "Mass Spectrometry and EST-Database Searching Allows Characterization of the Multi-Protein Spliceosome Complex", Nature Genetics, 1998, vol. 20, 46-50.
Neuhoff et al., "Improved Staining of Proteins in Polyacrylamide Gels Including Isoelectric Focusing Gels with Clear Background at Nanogram Sensitivity using Coomassie Brilliant Blue G-250 and R-250", Electrophoresis, 1988, vol. 9, 255-262.
Nielsen et al., "Acute Systemic and Local Inflammation Decreases Hepatic Expressions of Urea Cycle Enzymes", Journal of Hepatology, 2000, vol. 32 (Suppl. 2), 161.
Otto et al., "Identification of Human Myocardial Proteins Separated by Two-Dimensional Electrophoresis using an Effective Sample Preparation for Mass Spectrometry", Electrophoresis, 1996, vol. 17, 1643-1650.
Ozaki et al., "Enzyme-Linked Immunosorbent Assay of Carbamoylphosphate Synthetase I: Plasma Enzyme in Rat Experimental Hepatitis and its Clearance", Enzyme Protein, 1994, vol. 48(4), 213-221.
Redl et al., "Non-Human Primate Models of Sepsis", Sepsis, 1998, vol. 2, 243-253.
Redl et al., "Procalcitonin Release Patterns in a Baboon Model of Trauma and Sepsis: Relationship to Cytokines and Neopterin", Crit Care Med., 2000, vol. 28(11), 3659-3663.

(Continued)

*Primary Examiner* — Kagnew H Gebreyesus
(74) *Attorney, Agent, or Firm* — Heslin Rothenberg Farley & Mesiti P.C.

(57) ABSTRACT

The invention relates to the use of carbamoyl synthetase 1 (CPS 1) as a humoral biomarker in in vitro methods for early diagnosis and detection, progress prognosis, the evaluation of the severity, and the progress evaluation of tumor diseases and chronic inflammatory intestinal diseases.

3 Claims, 2 Drawing Sheets

OTHER PUBLICATIONS

Schimke, R., "Adaptive Characteristics of Urea Cycle Enzymes in the Rat", Journal of Biological Chemistry, 1962, vol. 237(2), 459-468.

Szondy et al., "Effect of Polyamines on the Carbamoylphosphate Synthetase Activity of Cad Protein", Database: BioSciences Information Service, 1989, vol. 24, 107-118.

Tabuchi et al., "Regulation of Genes for Inducible Nitric Oxide Synthase and Urea Cycle Enzymes in Rat Liver in Endotoxin Shock", Biochemical and Biophysical Research Communications, 2000, vol. 268(1), 221-224.

Tygstrup et al., "Expression of Liver Functions Following Sub-Lethal and Non-Lethal Doses of Allyl Alcohol and Acetaminophen in the Rat", Journal of Hepatology, 1997, vol. 27(1), 156-162.

Yin et al., "Participation of Different Cell Types in the Restitutive Response of the Rat Liver to Periportal Injury Induced by Allyl Alcohol", Journal of Hepatology, 1999, vol. 31(3), 497-507.

USE OF CARBAMOYL PHOSPHATE SYNTHETASE 1 (CPS) AS A HUMORAL BIOMARKER FOR THE DIAGNOSIS OF TUMOUR DISEASES AND CHRONIC INFLAMMATORY INTESTINAL DISEASES

This application claims priority to and is a continuation of co-pending U.S. application Ser. No. 11/575,603, filed Mar. 20, 2007, which is a §371 filing of PCT/EP05/09827, filed Sep. 13, 2005 (published as WO 06/032392), which claims the benefit of German Application No. 102004045705.0, filed Sep. 21, 2004. The entire content of each of the prior applications is incorporated herein by reference.

The present invention relates to novel uses of the enzyme carbamoyl phosphate synthetase 1 (E.C. 6.3.4.16, always abbreviated below to CPS 1) and/or physiologically occurring CPS 1 fragments having CPS 1 immunoreactivity as a humoral biomarker for medical diagnosis for the detection of tumour diseases (as a humoral tumour marker), i.e. for the diagnosis of tumour diseases, and for the detection and for the progress monitoring of chronic inflammatory intestinal diseases (Crohn's disease; Colitis ulcerosa), by detection of CPS 1 or CPS 1 immunoreactivity in the circulation, in particular in serum or plasma of patients on whom a routine examination to the possible presence of tumours/chronic inflammatory intestinal diseases is carried out, for whom there are grounds for suspecting tumours or chronic inflammatory intestinal diseases or in whom a tumour or a chronic inflammatory intestinal disease has already been detected and who are being monitored or subjected to a treatment.

In the context of the present application, the term "tumour" is used as an overall term or synonym for neoplasms, in particular malignant neoplasms, as are typical of cancer diseases (carcinomas). In a country like Germany, more than 300 000 men and women per year suffer from malignant neoplasms (malignant tumours), i.e. cancer, the number of new cancer cases diagnosed annually and the death rate being considerable. Malignant tumours may occur in virtually any tissue or organ, and, depending on the organ affected, a distinction is made between numerous cancer diseases which may differ considerably from one another with regard to their statistical frequency, prognosis and treatability.

Chronic inflammatory intestinal diseases, i.e. substantially Crohn's disease (also, Enteritis regionalis; abbreviated to C.D. in this application) and Colitis ulcerosa (abbreviated to C.U. in this application), which are intermittent chronic severe diseases with an aetiology not yet definitively explained, are closely related to tumour diagnosis in that it is known that these diseases exhibit malignant degeneration with a high percentage probability and lead to intestinal cancer.

Recent years have seen the development of a multiplicity of treatments which have brought considerable progress with respect to the curability of numerous forms of cancer diseases. In all cases, however it is true that the prospects of curing cancer diseases are always better the earlier the cancer disease is diagnosed. What is very particularly important thereby is early diagnosis of cancer at a time when as yet no significant clinical symptoms or none at all have occurred.

For the diagnosis of tumours as early as possible in clinical diagnosis, so-called "tumour markers" are determined in biological samples, in particular blood samples and body secretions, of patients examined. Tumour markers are substances which either are formed directly by malignant tumour cells or form as a result of tumour cells inducing the synthesis of the respective marker in non-tumour cells. Because tumour markers are detected in elevated concentration in fluid biological samples (humoral tumour markers) or locally in tissue (cellular tumour markers), they permit, depending on the given circumstances of the individual case, early diagnosis of malignant tumours in risk groups, they are used for primary tumour diagnosis and they permit prognosis and/or monitoring of a tumour treatment and optionally early diagnosis of recurrence of a tumour. In the present application, the term "diagnosis" is used as an overall term for all more special potential uses (indications) mentioned. An overview of the tumour markers currently used in clinical diagnosis is to be found in Lothar Thomas (editor), Labor and Diagnose, 5th extended edition, section 34, cf. in particular overview 34.1 "Maligne Erkrankungen [Malignant Diseases]" on pages 956-961, and the articles on individual clinically used tumour markers under 34.2-34.17 on pages 916-1019.

Common to all tumour markers determined at present is that the sensitivity of their determination is relatively limited and they have a relatively high organ specificity. The relatively high organ specificity of tumour markers determined at present has on the one hand the advantage that their detection simultaneously provides information about the organ in which the causative cancer disease has occurred with high probability. However, a high specificity is a disadvantage in that cancer diseases of other organs are not diagnosable in the determination of organ-specific tumour markers or the simultaneous determination of numerous different tumour markers is required for comprehensive early cancer diagnosis. The relatively low sensitivity of the determination of the known tumour markers (in the case of a high sensitivity of a determination, most or all patients are correctly diagnosed), which is between 20 and 80% depending on cancer disease and tumour marker, results in the danger of non-diagnosis of cancer diseases still being very high in spite of the determination of the tumour markers suitable per se for this purpose.

Chronic inflammatory intestinal diseases initially frequently have uncharacteristic symptoms which make reliable early diagnosis more difficult. A biomarker which permits clear linkage of the symptoms with the correct diagnosis "chronic inflammatory intestinal disease" or CD or CU would therefore be very much welcomed by those skilled in the art. If such a biomarker is linked to the severity of the pathogenic episodes, it could be very advantageous in monitoring progress and treatment.

There is therefore still a need for novel humoral biomarkers, in particular humoral tumour markers and humoral markers for chronic inflammatory intestinal diseases, which, on the basis of a characteristic organ specificity or sensitivity of their own, permit improved diagnosis, in particular cancer diagnosis, either in their determination alone or in combination with the determination of one or more other biomarkers/tumour markers.

The present invention relates to the identification of a humoral biomarker which can serve as a novel humoral tumour marker and a novel biomarker for chronic inflammatory intestinal diseases, and all possible uses arising from its identification in the area of tumour diagnosis and the diagnosis of chronic inflammatory intestinal diseases.

The Claims are intended to provide protection under patent law for these uses or in vitro diagnosis methods with determination of the novel humoral tumour marker or humoral biomarker for chronic inflammatory intestinal diseases.

The present invention is based on the surprising finding that substantially elevated concentrations of the enzyme carbamoyl phosphate synthetase 1 (CPS 1) or strong CPS 1 immunoreactivity were detectable with in some cases outstanding sensitivity in the circulation, i.e. in particular in plasmas or sera, of patients in whom clinically different tumours, in particular of internal organs or soft tissues, had been identified, and of patients with C.D or C.U., in clear contrast to healthy control persons, which makes CPS 1 or CPS 1 immunoreactivity a novel humoral tumour marker or biomarker for chronic inflammatory intestinal diseases.

With the use of an immunoassay which had been developed in relation to sepsis diagnosis and which selectively permits the detection or the measurement of CPS 1 or CPS 1 immunoreactivity in a serum or plasma of a human patient, the Applicant found that CPS 1 or a strong CPS immunoreactivity can be found in greatly elevated concentrations also in the circulation of patients with various clinically diagnosed tumours.

As part of the same investigation, it was furthermore found that the same biomarker is also present at a substantially elevated level in the circulation of patients with chronic inflammatory intestinal diseases (C.D; C.U.), in particular during the acute pathogenic episodes typical of these diseases.

CPS 1 or CPS 1 fragments with CPS 1 immunoreactivity traditionally played no practical role for medical diagnosis. In the narrower relevant area of tumour diagnosis, CPS 1 has as yet never been discussed as a possible humoral tumour marker.

The enzyme CPS 1 (E.C. 6.3.4.16) itself has, however, long been well known. It catalyzes the conversion of ammonia, bicarbonate and 2 ATP with formation of carbamoyl phosphate in the first step of the urea cycle. It also plays a role in the biosynthesis of arginine, which in turn is a substrate for the biosynthesis of NO, e.g. in the case of an endotoxin shock (c.f. Shoko Tabuchi et al., Regulation of Genes for Inducible Nitric Oxide Synthase and Urea Cycle Enzymes in Rat Liver in Endotoxin Shock, Biochemical and Biophysical Research Communications 268, 221-224 (2000)). CPS 1 should be distinguished from the cytosolic enzyme CPS 2 (E.C. 2.7.2.5.), which likewise plays a role in the urea cycle but processes the substrate glutamine. It is known that CPS 1 is localized in mitochondria and occurs in this form in large amounts in liver tissue (it accounts for 2-6% of total liver protein). Its amino acid sequence and genetic localization have long been known (c.f. Haraguchi Y. et al., Cloning and sequence of a cDNA encoding human carbamyl phosphate synthetase I: molecular analysis of hyperammonemia, Gene 1991, Nov. 1; 107 (2); 335-340; cf. also the publication WO 03/089933 A1 of the Applicant). Regarding its physiological role, reference may be made to review articles such as, for example, H. M. Holder et al., Carbamoyl phosphate synthetase: an amazing biochemical odyssey from substrate to product, CMLS, Cell. Mol. Life Sci. 56 (1999) 507-522, and the literature referred to therein, and the introduction to the publication by Mikiko Ozaki et al., Enzyme-Linked Immunosorbent Assay of Carbamoylphosphate Synthetase I: Plasma Enzyme in Rat Experimental Hepatitis and Its Clearance, Enzyme Protein 1994, 95:48:213-221.

According to Shoko Tabuchi et al., loc. cit., no increase in the enzyme (protein) is observed in rat livers in the case of an artificial endotoxin shock (LPS). According to Li Yin et al., Participation of different cell types in the restitutive response of the rat liver to periportal injury induced by allyl alcohol, Journal of Hepatology 1999, 31:497-507, an increase in CPS 1 expression can be observed in the case of liver damage by allyl alcohol in histological examinations after three days in all hepatocytes.

It was furthermore found that, in the rat model, greatly increased immunological CPS 1 activity is found in the rat plasma in acute hepatitis induced experimentally by administering galactosamine (detected using an ELISA with anti-rat CPS 1 IgG from rabbit), in particular 24-48 h after the treatment with the hepatitis-inducing galactosamine. In the rat plasma, CPS 1 fragments having molar masses of about 140 and 125 kDa were also increasingly detectable during the acute hepatitis, without other more detailed characterization (sequence assignment), whereas no CPS 1 fragments with CPS 1 immunoreactivity could be observed in human autopsy samples in an accompanying immunoblotting analysis (Mikiko Ozaki et al., loc. cit.).

A paper by Liu Tong-hua et al., Carbamoyl Phosphate Synthetase 1, A Novel Marker for Gastric Carcinoma, Chinese Medical Journal, 102 (8):630-638, 1989, reports results of immunocytometric investigations of tissue samples from various surgically removed tumours for possible presence of CPS 1. The authors found indications of CPS 1 immunoreactivity only in carcinoma tissue from the stomach, but not in other tumour tissues (oesophagus, large intestine, pancreas, lung, breast, ovary, kidney, prostate and bladder). They derive therefrom a possible suitability of CPS 1 as a selective tissue marker, i.e. cellular tumour marker, for gastric cancer. A possible occurrence of CPS 1 in the circulation is not discussed, and no conclusions at all can be drawn from the described investigations with regard to a possible suitability of CPS 1 as a humoral tumour marker.

The measurements described in the present application constitute the first report about the occurrence of CPS 1 in the circulation of tumour patients and patients with chronic inflammatory intestinal diseases. To date, CPS 1 has been determined only in serum or plasma of sepsis patients, and also only in investigations by the Applicant (cf. WO 03/089933 A1). Sepsis patients whose highly acute potentially life-threatening disease is typically monitored and treated in intensive care wards represent a patient population which clearly differs from tumour patients, tumour risk patients or patients with chronic inflammatory intestinal diseases, i.e. patients who are suffering from a disease developing over long periods or chronic disease.

In the determination of CPS 1 or CPS 1 immunoreactivity as a humoral biomarker/tumour marker in patient sera according to the present invention, it is possible in principle to proceed as described in the publication WO 03/089933 A1 of the Applicant in relation to the determination of CPS 1 as a sepsis marker. The assay method which is described in the experimental section of the present application and which was used for the testing of sera or plasmas of tumour patients for the presence of CPS 1 or CPS 1 immunoreactivity is the same method as that already described in the above-mentioned Application WO 03/089933 A1 of the Applicant.

In the context of the present application, "use" is to be regarded as not only the direct immunological determination of CPS 1 in in vitro samples in tumour diagnosis and diagnosis of chronic inflammatory intestinal diseases but also a use of CPS 1 or CPS 1 fragments, or of antibodies to the selective determination thereof, for the preparation of assay kits, or a use for the production of assay components, e.g. of polyclonal or monoclonal antibodies which are provided, for example, in immobilized and/or marked form, as a rule likewise in assay kits for said diseases, or of standard and reference substances.

It should also expressly be pointed out that, in the determination of CPS 1 or CPS 1 immunoreactivity according to the invention, depending on the assay design, a simultaneous determination of CPS 1 both in the form of the substantially complete molecule and in the form of other, shorter fragments (physiologically occurring partial peptides) of the complete CPS 1 which are possibly present in the biological fluid can take place. When a determination of "CPS 1 immunoreactivity" is mentioned in the present application, this should take account of this measuring situation so that an improper restrictive interpretation of the teaching of the present invention is avoided.

Instead of the determination of CPS 1 or CPS 1 immunoreactivity, it should be possible, for diagnostic purposes, optionally also to effect the CPS 1 determination indirectly as a determination of an enzyme activity which corresponds to the CPS 1 activity or the residual activity of the CPS 1 fragments in the blood. Since CPS 1 in healthy persons does not occur in the circulation, a measurable CPS 1 enzyme activity in the blood of a patient may be a diagnostically significant indication of a serious disturbance of the unimpaired health of the patient. It should also be pointed out here that the activity of an enzyme which is normally localized in the interior of the cell and displays its proper function only there is to be rated as negative per se in the circulation and as such can therefore also contribute to a worsening of the condition.

CPS 1 and CPS 1 immunoreactivity detectable in plasma and serum are suitable, on the basis of the results described below, as specific marker peptides (tumour markers) for the diagnosis of tumours (neoplasms) and for the detection and for the monitoring of progress and treatment of C.D. or C.U.

It is furthermore intended to carry out the determination of CPS 1 and/or CPS 1 fragments as prognosis markers and markers for the monitoring of the progress of tumour diseases as part of a combination measurement with other markers.

The actual CPS 1 determination can be effected in any suitable manner known per se, immunoassays of a suitable assay design being preferred.

The method for determining CPS 1-immunoreactivity in a biological sample may be any desired known methods of immunodiagnosis which are used for the detection and for the measurement of antigens. Preferably, CPS 1 is determined with the aid of a ligand binding assay in which specific antibodies suitable for binding and marking are used in immobilized form or marked or markable form.

Competitive assay formats may also have particular advantages. Preferably, instead of employing enzyme marking, another marking is chosen, e.g. marking for a chemiluminescence detection reaction, e.g. an acridinium ester. Of course, it is preferable to use for the CPS 1 determination an assay which ensures the required high sensitivity in the range of the CPS 1 concentrations occurring and permits a separation of the measured signals from the assay background.

The assay method can be adapted to chip technology or can be designed as an accelerated test (point-of-care test).

In a preferred embodiment, the immunodiagnostic determination is carried out as a heterogeneous sandwich immunoassay in which one of the antibodies is immobilized on any desired solid phase, for example the walls of coated test tubes (e.g. of polystyrene; "coated tubes"; CT) or on microtitre plates, for example of polystyrene, or on particles, for example magnetic particles, while the other antibody carries a residue which represents a directly detectable label or permits a selective link to a label and serves for the detection of the sandwich structures formed. Delayed or subsequent immobilization with the use of suitable solid phases is also possible.

In principle, it is possible to use all marking techniques which can be used in assays of the described type and which comprise markings with radio isotopes, enzymes or fluorescent, chemiluminescent or bioluminescent labels and directly optically detectable colour markings, such as, for example, gold atoms and dye particles, as used in particular for so-called point-of-care (POC) or accelerated tests. In the case of heterogeneous sandwich immunoassays, the two antibodies may also have parts of a detection system of the type described below in relation to homogeneous assays.

The method according to the invention can furthermore be designed as a homogeneous method in which the sandwich complex formed from the two antibodies and the CPS 1 to be detected remain suspended in the liquid phase. In such a case, it is preferably to mark both antibodies with parts of a detection system, which permits signal generation or signal triggering when both antibodies are integrated into a single sandwich. Such techniques can be designed in particular as fluorescence amplification or fluorescence extinction detection methods. A particularly preferred method of this type relates to the use of detection reagents to be used in pairs, as described, for example, in U.S. Pat. No. 4,822,733, EP-B1-180 492 or EP-B1-539 477 and the prior art cited therein. They permit a measurement which selectively detects only reaction products which contain both marking components in a single immune complex directly in the reaction mixture. As an example, reference may be made to the technology offered under the brands TRACE® (Time Resolved Amplified Cryptate Emission) and KRYPTOR®, which implement the teachings of the above-mentioned applications.

The content of said prior application (WO 03/089933 A1) of the Applicant is to be regarded as part of the disclosure of the present application by incorporation of these applications by reference.

Below, the determination of CPS 1 and the findings obtained in their determination in plasmas of tumour patients and patients with C.D. or C.U. are explained in more detail, reference being made to two figures.

There:

EXPERIMENTAL SECTION

Figure 1:
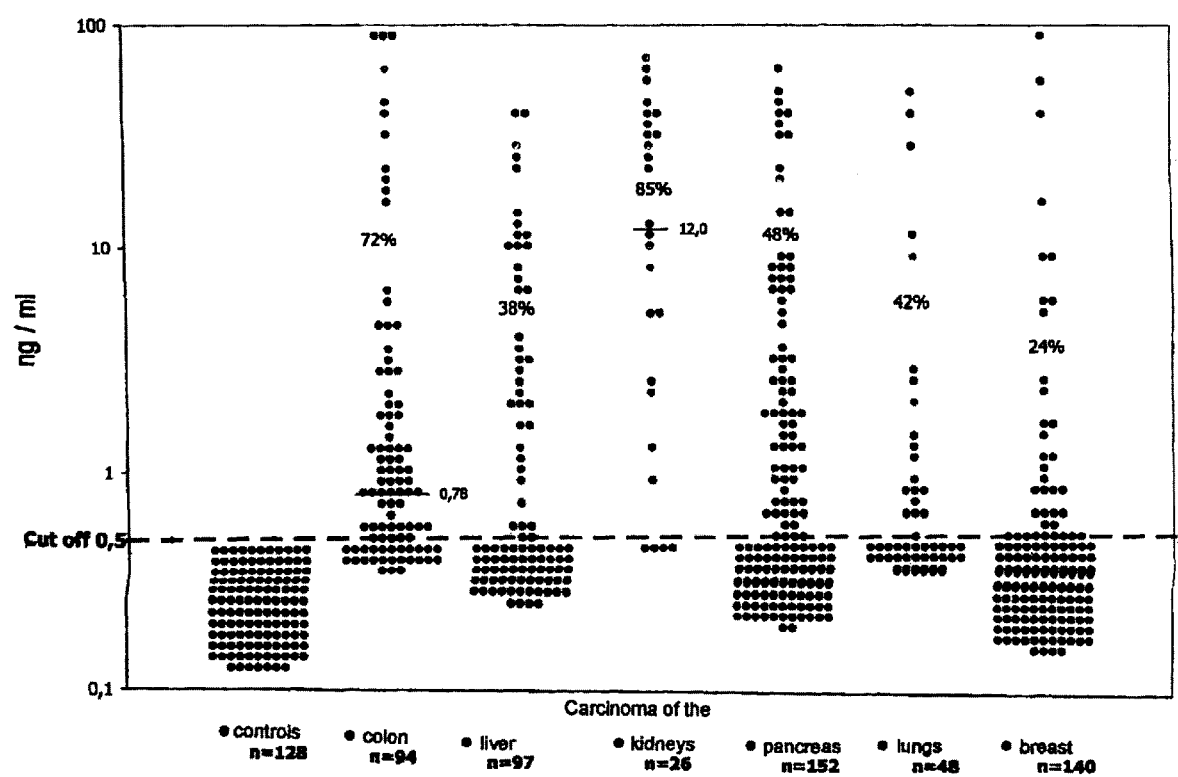
FIG. 1 shows the results of the measurement of the CPS 1 immunoreactivity in plasmas of healthy normal persons and of patients with various, clinically diagnosed tumour diseases indicated in the figure by the immunoassay described in more detail in the experimental section, the dashed line indicating the lower limit of detection of the test (0.5 ng/ml).

CPS 1 immunoreactivity determinations in human plasmas of healthy normal persons and tumour patients
1. Material and Methods
1.1 Peptide Syntheses Derived from the known amino acid sequence of human CPS 1, two ranges were selected (Pos. 184-199: Peptide range 1; SEQ ID NO:1; Pos. 245-257: Peptide range 1; SEQ ID NO 2). Supplemented in each case by an N-terminal cysteine residue, both ranges were chemically synthesised by standard methods as soluble peptides, purified, subjected to quality control by means of mass spectrometry and reversed phase HPLC and lyophilized in aliquots (JERINI AG, Berlin, Germany). The amino acid sequences of the peptides were as follows:

```
Peptide PCEN17:
CEFEGQPVDFVDPNKQN         SEQ ID NO: 1

Peptide PCVD14:
CVPWNHDFTKMEYD            SEQ ID NO: 2
```

Recombinant standard material was obtained from InVivo GmbH (Henningsdorf, Germany). This was a crude cell extract of an *E. coli* strain which expressed the recombinant N-terminal region of human CPS 1, supplemented by an N-terminal strip of strep tag. An arbitrary concentration of CPS 1 was attributed to the extract.

1.2 Conjugation and Immunisation

The abovementioned peptides PCEN17 and PCVD14 were conjugated with the carrier protein KLH (keyhole limpet hemocyanine) by means of MBS (m-maleimidobenzoyl-N-hydroxysuccinimide ester) (cf. operating procedure "NHS-Esters-Maleimide Crosslinkers" from PIERCE, Rockford, Ill., USA). Sheep were immunized with these conjugates according to the following scheme: Each sheep initially received 100 µg of conjugate (stated mass based on the peptide fraction of the conjugate) and then 50 µg of conjugate every 4 weeks (stated mass based on the peptide fraction of the conjugate). Beginning with the 4th month after the beginning of immunisation, 700 ml of blood were taken per sheep every 4 weeks and antiserum was obtained therefrom by centrifuging. Conjugations, immunisations and recovery of antisera were carried out by MicroPharm, Carmarthenshire, UK.

1.3 Purification of the Antibody

The peptide-specific antibodies were prepared in a 1-step method from the antisera which had been obtained beginning with the fourth month after immunisation.

For this purpose, the peptides PCEN17 and PCVD14 were first coupled with Sulfo-Link gel (cf. operating procedure "SulfoLink Kit" from PIERCE, Rockford, Ill., USA). In each case 5 mg of peptide were offered per 5 ml of gel for coupling.

The affinity purification of peptide-specific antibodies from sheep antisera against both peptides was carried out as follows:

The peptide columns were first washed three times alternately with 10 ml each of elution buffer (50 mM citric acid, pH 2.2) and binding buffer (100 mM sodium phosphate, 0.1% Tween, pH 6.8). 100 ml of the antisera were filtered over 0.2 µm and the column material present was added. For this purpose, the gel was quantitatively rinsed with 10 ml of binding buffer from the column. The incubation was effected overnight at room temperature with tilting. The batches were transferred quantitatively into empty columns (NAP 25, Pharmacia, emptied). The run-throughs were discarded. Washing was then carried out with 250 ml of binding buffer until protein-free (protein content of the wash eluate <0.02 A280 nm). Elution buffer was added to the washed columns, and 1 ml fractions were collected. The protein content of each fraction was determined by means of the BCA method (cf. operating procedure of PIERCE, Rockford, Ill., USA). Fractions having protein concentrations >0.8 mg/ml were pooled. Protein determination of the pools by means of the BCA method gave yields of 27 mg for the anti-PCEN17 antibody and 33 mg for the anti-PCVD14 antibody.

1.4 Marking

500 µl of the purified anti-PCEN17 antibody (see above) were rebuffered with 1 ml of 100 mM potassium phosphate buffer (pH 8.0) via an NAP-5 gel filtration column (Pharmacia) according to the operating procedure. The protein concentration determination of the antibody solution gave a value of 1.5 mg/ml.

For the chemiluminescence marking of the antibody, 10 µl of MA70 acridinium NHS ester (1 mg/ml; from HOECHST Behring) were added to 67 µl of the antibody solution and incubation was effected for 15 minutes at room temperature. 423 µl of 1 M glycine were then added and incubation was effected for a further 10 minutes. Thereafter, the marking batch was rebuffered via an NAP-5 gel filtration column (Pharmacia) with 1 ml of mobile phase A (50 mM potassium phosphate, 100 mM NaCl, pH 7.4) according to the operating procedure and was freed from low molecular weight constituents. A gel filtration HPLC was carried out for separating off final residues of labels not bound to antibodies (column: Waters Protein Pak SW300). The sample was applied and was chromatographed at a flow rate of 1 ml/min with mobile phase A. The wavelengths 280 nm and 368 nm were measured using a flow photometer. The absorption ratio 368 nm/280 nm as a measure of the degree of marking of the antibody was 0.10 at the peak. The monomeric fractions containing antibodies (retention time 8-10 min) were collected and were collected in 3 ml of 100 mM sodium phosphate, 150 mM NaCl, 5% bovine serum albumin, 0.1% sodium azide, pH 7.4.

1.5 Coupling

Irradiated 5 ml polystyrene tubes (from Greiner) were coated with purified anti-PCVD14 antibody as follows: the antibody was diluted in 50 mM Tris, 100 mM NaCl, pH 7.8 to a concentration of 6.6 µg/ml. 300 µl of solution were pipetted into each cube. The tubes were incubated for 20 hours at 22° C. The solution was filtered with suction. Each tube was then filled with 4.2 ml of 10 mM sodium phosphate, 2% Karion FP, 0.3% bovine serum albumin, pH 6.5. After 20 hours, the solution was filtered with suction. Finally, the tubes were dried in a vacuum dryer.

2. Procedure and Evaluation of the Immunoassay 2.1 Assay Design

An assay buffer of the following composition was prepared:

100 mM sodium phosphate, 150 mM NaCl, 5% bovine serum albumin, 0.1% unspecific sheep IgG, 0.1% sodium azide, pH 7.4

The standard material used was recombinant human CPS 1 expressed in *E. coli*, in the form of a crude *E. coli* extract, containing the total soluble intracellular protein. This extract was diluted serially in horse normal serum (from SIGMA). Arbitrary concentrations were attributed to the standards thus prepared, according to their dilution.

2.2 Measurement of EDTA Plasmas of Apparently Healthy Persons and of Patients with Various Neoplasms (Tumours) Test Sera:

a. Test sera used for the CPS 1 determinations were firstly 557 plasmas of various patients with clinically diagnosed tumours of various organs/tissues. For each test plasma there existed exact clinical documentation which permitted an itemisation of the patient plasmas used in the measurement according to the tumour type found in them.

More precisely, the following were measured: 94 plasmas of patients with cancer of the large intestine (in FIG. 1: Colon-Ca), 97 plasmas of patients with liver cancer (Liver-Ca), 26 plasmas of patients with kidney cancer (Kidney-Ca), 152 plasmas of patients with pancreatic cancer (Pancreas-Ca), 48 plasmas of patients with lung cancer (Lung-Ca) and 140 plasmas of patients with breast cancer (Breast-Ca).

Figure 2:
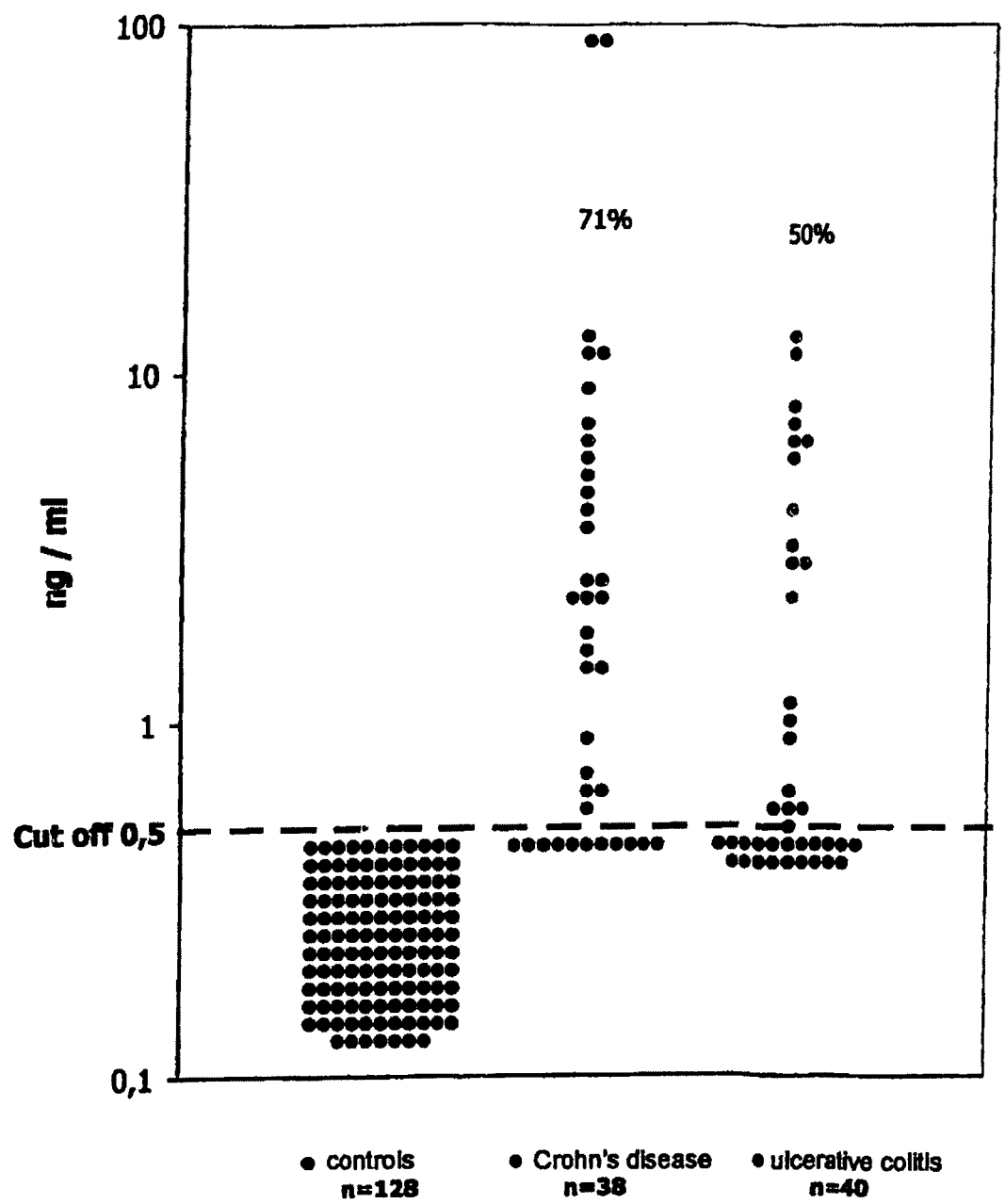
FIG. 2 shows corresponding results in plasmas of patients who are suffering from an acute episode of their chronic inflammatory intestinal disease (C.D. or C.U.).

Control sera used were 128 sera of apparently healthy persons.

b. Sera of 78 patients altogether for whom treatment of an acute episode of Crohn's disease (C.D.) or Colitis ulcerosa (C.U.) was carried out were also measured at the same time (FIG. 2).

50 µl each of standard and sample and 200 µl of assay buffer were pipetted into the abovementioned test tubes. Incubation was effected for 18 hours at 22° C. with shaking. Washing was then effected 4 times with 1 ml of wash solution (0.1% Tween 20) per tube each time. 200 µl of assay buffer, containing 0.5 million RLU of the MA70-marked tracer antibody, were then pipetted into each tube. Incubation was effected for two hours at 22° C. with shaking. Washing was then effected 4 times with 1 ml of wash solution (0.1% Tween 20) per tube each time, the tubes were allowed to drip and the chemiluminescence bound to the tube was measured in a luminometer (from BERTHOLD, LB952T; base reagents from BRAHMS AG).

The concentration of CPS 1 immunoreactivity was read using the MultiCalc (spline fit) software. The results for tumour patients are shown in FIG. 1 and the results for patients with chronic inflammatory intestinal diseases (C.D.; C.U.) are shown in FIG. 2. In each case, a clear difference is found between healthy persons, in whom no concentrations of CPS 1 above the limit of detection (0.5 ng/ml) were found, and patients, the sensitivity of the detection of CPS 1 being entirely different for different tumour types.

In particular, the following sensitivities were determined for the various cancer types (cf. FIG. 1):

| | |
|---|---|
| Cancer of the large intestine | 72% |
| Liver cancer | 38% |
| Kidney cancer | 85% |
| Pancreatic cancer | 48% |
| Lung cancer | 42% |
| Breast cancer | 24%. |

The sensitivity in the case of inflammatory intestinal diseases (Crohn's disease/Colitis ulcerosa) was 71% for C.D. and 50% for C.U.

By means of the sandwich immunoassay described, it was thus shown that plasmas of tumour patients and patients in an acute phase of a chronic inflammatory intestinal disease can have greatly increased concentrations of CPS 1 immunoreactivity, whilst CPS 1 was not detectable in plasmas of healthy persons. An enormous increase in the CPS 1 immunoreactivity in plasma was found for various tumour patients. This cannot be related in any clear logical manner to the previously known occurrence of CPS 1 in sepsis. It is known that damage to the mitochondria occurs in the case of sepsis (Crouser E D et al., Endotoxin-induced mitochondrial damage correlates with impaired respiratory activity; Crit. Care Med. 2002 February; 30(2):276-84). Such damage in combination with necrosis or apoptosis could be a cause of the passage of CPS 1 from the mitochondrial matrix into the blood circulation in the case of sepsis. However, this assumption for explaining the occurrence of CPS 1 in the case of sepsis does not provide a simple plausible explanation for the occurrence in sera or plasmas of tumour patients, which was not predictable on the basis of the discoveries of the prior art.

The discoveries on which the present invention is based, concerning the occurrence of considerable concentrations of CPS 1 in the circulation of cancer patients and C.D. or C.U. patients make it appear possible that, even in dissolved form, CPS 1 has retained at least some of its enzyme reactivity and contributes to a worsening of the disease and/or to certain undesired consequences of the disease. Moreover, it is found that substances known per se which inhibit the expression or the enzymatic activity of CPS 1 may be suitable for positively influencing the overall pathological process. Such substances are described, for example, in J. Steroid Biochem Mol Bio 1991 May; 38(5):599-609; J Biol Chem 1977 May 25; 252 (10):3558-60; J Biol Chem 1984 Jan. 10; 259(1):323-31 and J Biol Chem 1981 Nov. 10; 256(21):1160-5; J Biol Chem 1981 Apr. 10; 256(7):3443-6. They include in particular Ca ions and other metal ions and substances of the steroid type. They furthermore include antibodies or other specific binders which, as CPS 1 inhibitors, can eliminate or reduce the activity of CPS 1 in the circulation by binding to CPS 1.

Accordingly the administration of such CPS 1 inhibitors to patients in whom CPS 1 is detectable in the blood is a means of therapeutically influencing the pathological process and significantly improving the condition and/or the wellbeing of a cancer patient. A further teaching based on the fundamental discoveries of the present invention is therefore to provide CPS 1 inhibitors as active constituents of therapeutic agents which are intended for the treatment of cancer patients and of patients who are suffering from an acute episode of C.D. or C.U.

The invention claimed is:

1. A method for the diagnosis of a tumor disease, said method comprising:
   determining the level of human carbamoyl phosphate synthetase 1 (CPS 1) and/or physiologically occurring fragments that retain human CPS 1 immunoreactivity in a serum or plasma sample of a human patient using an immunoassay that uses a first antibody that binds to a first peptide consisting of the sequence of SEQ ID NO:1, and a second antibody that binds to a second peptide consisting of the sequence of SEQ ID NO:2; and
   comparing the level of human CPS 1 and/or CPS1 fragments that retain CPS 1 immunoreactivity in said sample with the level in normal individuals, wherein an increased level compared to normal individuals indicates a tumor disease.

2. The method of claim 1, wherein said tumor disease is selected from the group consisting of carcinomas of the large intestine, kidney carcinomas pancreatic carcinomas, lung carcinomas and breast carcinomas and combinations thereof.

3. A method for assisting in the detection and diagnosis of a tumor disease selected from the group consisting of carcinomas of the large intestine, kidney carcinomas, pancreatic carcinomas, lung carcinomas and breast carcinomas and combinations thereof, said method comprising:
   determining in a serum or plasma sample of a human patient the level of human carbamoyl phosphate synthetase 1 (CPS 1) and/or physiologically occurring fragments of CPS 1 that retain human CPS 1 immunoreactivity using an immunoassay that uses a first antibody that binds to a first peptide consisting of the sequence of SEQ ID NO: 1, and a second antibody that binds to a second peptide consisting of the sequence of SEC ID NO: 2; and
   comparing the level of human CPS 1 and/or CPS1 fragments that retain CPS 1 immunoreactivity in said sample with the level in normal individuals, wherein an increased level compared to normal individuals indicates a tumor disease selected group consisting of carcinomas of the large intestine, liver carcinomas, kidney carcinomas, pancreatic carcinomas, lung carcinomas and breast carcinomas and combinations thereof.

\* \* \* \* \*

SEQUENCE LISTING

<160> NUMBER OF SEQ ID NOS: 2

<210> SEQ ID NO 1
<211> LENGTH: 17
<212> TYPE: PRT
<213> ORGANISM: Artificial
<220> FEATURE:
<221> NAME/KEY: misc_feature
<222> LOCATION: (1)..(17)
<223> OTHER INFORMATION: synthetic peptide

<400> SEQUENCE: 1

Cys Glu Phe Glu Gly Gln Pro Val Asp Phe Val Asp Pro Asn Lys Gln
1               5                   10                  15

Asn

<210> SEQ ID NO 2
<211> LENGTH: 14
<212> TYPE: PRT
<213> ORGANISM: Artificial
<220> FEATURE:
<221> NAME/KEY: misc_feature
<222> LOCATION: (1)..(14)
<223> OTHER INFORMATION: synthetic peptide

```
<400> SEQUENCE: 2

Cys Val Pro Trp Asn His Asp Phe Thr Lys Met Glu Tyr Asp
1               5                   10
```